United States Patent
Kuhns

[11] Patent Number: 5,997,533
[45] Date of Patent: Dec. 7, 1999

[54] RF PRESSURE ACTIVATED INSTRUMENT

[75] Inventor: Jesse J. Kuhns, Cincinnati, Ohio

[73] Assignee: Ethicon Endo-Surgery, Inc., Cincinnati, Ohio

[21] Appl. No.: 09/016,811

[22] Filed: Jan. 30, 1998

[51] Int. Cl.[6] .................................................. A61B 17/36
[52] U.S. Cl. ............................... 606/41; 606/42; 606/48; 606/50
[58] Field of Search ................................ 606/34, 41–52; 600/372–381; 607/116, 119, 122

[56] References Cited

U.S. PATENT DOCUMENTS

| | | | |
|---|---|---|---|
| 2,031,682 | 2/1936 | Wappler et al. | 174/89 |
| 2,056,377 | 10/1936 | Wappler | 128/303.14 |
| 2,137,710 | 11/1938 | Anderson | 128/321 |
| 3,970,088 | 7/1976 | Morrison | 128/303.14 |
| 4,043,342 | 8/1977 | Morrison | 128/303.14 |
| 4,418,692 | 12/1983 | Guay | 128/303.14 |
| 4,625,723 | 12/1986 | Altnether et al. | 128/303.1 |
| 4,711,239 | 12/1987 | Sorochenko et al. | 128/303.14 |
| 4,823,791 | 4/1989 | D'Amelio et al. | 123/303.14 |
| 5,009,656 | 4/1991 | Reimels | 606/48 |
| 5,047,027 | 9/1991 | Rydell | 606/48 |
| 5,078,717 | 1/1992 | Parins et al. | 606/48 |
| 5,217,458 | 6/1993 | Parins | 606/48 |
| 5,250,047 | 10/1993 | Rydell | 606/48 |
| 5,277,696 | 1/1994 | Hagen | 606/49 |
| 5,281,216 | 1/1994 | Klicek | 606/42 |
| 5,335,668 | 8/1994 | Nardella | 128/734 |
| 5,352,222 | 10/1994 | Rydell | 606/37 |
| 5,599,347 | 2/1997 | Hart et al. | 606/42 |
| 5,674,220 | 10/1997 | Fox et al. | 606/51 |
| 5,772,660 | 6/1998 | Young et al. | 606/42 |
| 5,776,130 | 7/1998 | Buysse et al. | 606/48 |

OTHER PUBLICATIONS

Rondinone J., Brassell J., Miller III S., Thorne J., Rondinone D., Safabash J., Vega F. (1998) A New Electrosurgical Ball Electrode with NOn–Stick Properties. SPIE vol. 3249 142–146.

*Primary Examiner*—Linda C. M. Dvorak
*Assistant Examiner*—David M. Ruddy
*Attorney, Agent, or Firm*—Louis J. Capezzuto

[57] ABSTRACT

An electrosurgical instrument includes a housing and a first connector in the housing for receiving electrical energy. A shaft assembly is movably connected to the housing. The shaft assembly also includes at least one electrode at a distal end of the shaft assembly as well as at least one conductive portion for passing the electrical energy to the electrode. A spring is positioned between the shaft assembly and the housing for biasing the shaft assembly a distance away from the first connector. The distance defines a pre-determined gap between the first connector and the shaft assembly. The shaft assembly is proximally movable in the housing upon an application of force at the shaft assembly distal end for compressing the spring such that the conductive portion traverses the predetermined gap such that electrical energy is passed from the first connector to the electrode through the conductive portion.

27 Claims, 6 Drawing Sheets

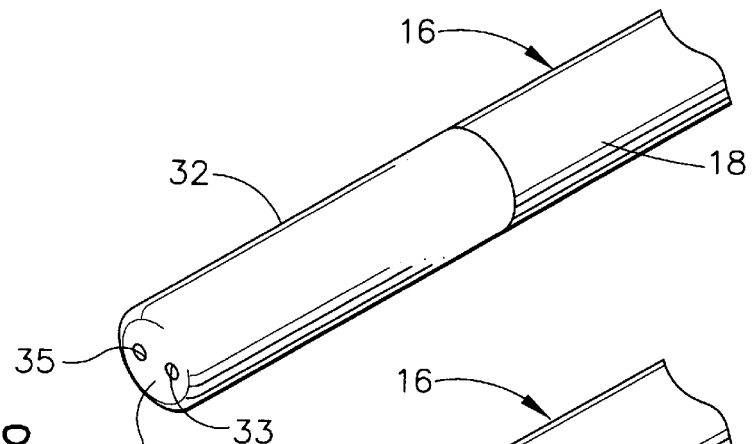
FIG. 8
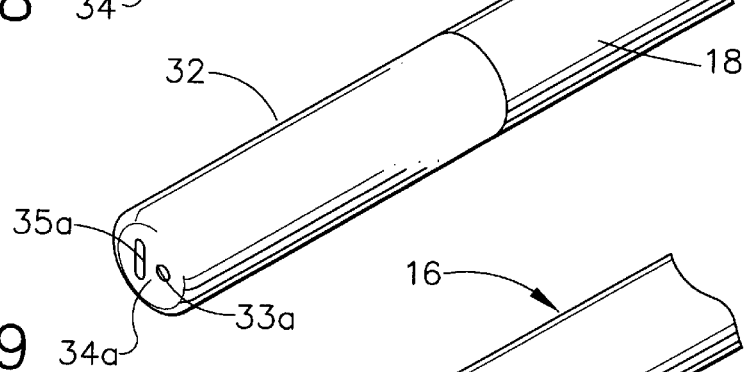
FIG. 9
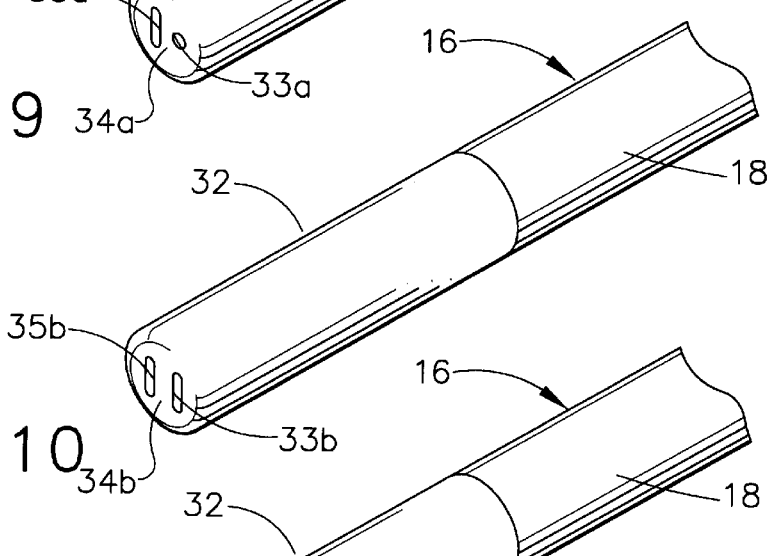
FIG. 10
FIG. 11
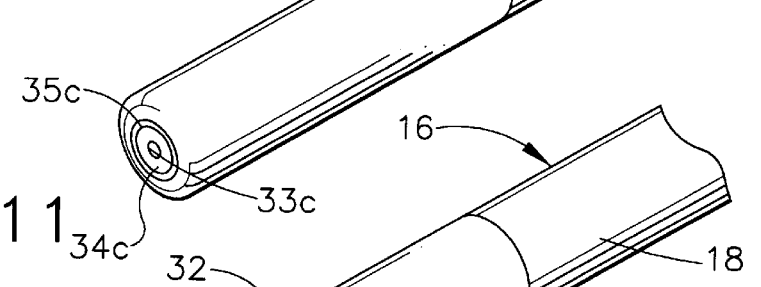
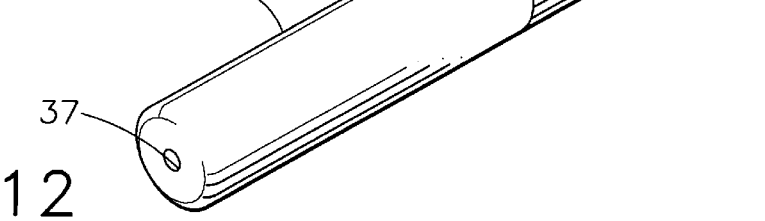
FIG. 12

RF PRESSURE ACTIVATED INSTRUMENT

FIELD OF THE INVENTION

The present invention relates, in general, to electrosurgical devices, and more particularly, to a new useful electrosurgical pressure instrument that applies radio frequency (RF) energy to tissue or material upon an application of force to the distal end of the instrument.

BACKGROUND OF THE INVENTION

It is well established in the surgical field to use RF energy to perform therapeutic activities such as coagulate, dessicate, cut, cauterize, or dissect tissue. Accordingly, the use of RF energy is common in various types of surgical instruments. Additionally, it is common practice to use RF electrosurgical instruments that are either monopolar or bipolar.

Generally, in monopolar RF electrosurgical instruments, a single pole, such as an electrode, is located on the instrument for transmitting RF energy from a power source through the patient to a second pole, normally a grounding pad, which is located at an exterior portion of the patient's body. Since the grounding pad is connected to the power source, this energy transmission results in a complete electrical circuit. Only that tissue at or immediately near the instrument electrode receives the RF energy for performing one of the therapeutic actions outlined above.

In bipolar RF electrosurgical instruments, first and second poles, normally two electrodes, are located in close proximity to each other such that RF energy is transmitted from a power source to the first electrode through tissue to the second electrode, and returned through a conductive return path in the instrument. Bipolar RF instruments provide a complete circuit when activated and only that tissue located between the two poles is substantially effected by the therapy. Collateral tissue effects are experienced at adjacent tissue immediately located at each pole.

Some widely known examples of monopolar and bipolar RF electrosurgical instruments are outlined below. For example, U.S. Pat. No. 4,625,723 to Altnether et al., describes an electrosurgical monopolar RF pencil having a relatively flat spatula blade for cutting and coagulating tissue.

Another type of RF electrosurgical instrument is a pair of bipolar electrosurgical scissors such as those described in U.S. Pat. No. 5,352,222 to Rydell. Each scissor blade is a distinct pole or electrode for effecting coagulation and cutting of tissue between the blades. It is also common for electrosurgical scissors to be used as a monopolar device in conjunction with a grounding pad.

U.S. Pat. No. 4,418,692 to Guay describes electrosurgical forceps for use as a tubal cauterization and ligation device. This device can be used as either a monopolar or a bipolar device. Upon activation of a button, the jaws or electrodes of the forceps are closed around a structure, such as a fallopian tube, by releasing compression of a spring causing contact arms of a piston to contact conductive pads for completing the electrical circuit. This particular design is used as a safety feature to prevent electrification of the electrodes when they are in the open position.

U.S. Pat. No. 2,031,682 to Wappler et al. discloses electrosurgical forceps that can be either monopolar or bipolar. The device includes one fixed jaw and one pivotal jaw with an electrified cutting wire. Both jaws are open loop configurations which permit the cutting wire to travel into the open portions for coagulating and cutting tissue contained between the jaws.

U.S. Pat. No. 5,674,220 to Fox et al. describes a bipolar forceps device that also utilizes two jaws having an open loop configuration. A mechanical cutting blade is advanced into the open area to cut the coagulated tissue after the jaws have been energized and the tissue has been coagulated to the surgeon's satisfaction.

Another type of electrosurgical device is shown in U.S. Pat. No. 4,043,342 to Morrison, Jr. The device utilizes an active cutting electrode, such as a needle, which is spring biased such that the needle is forced deeper into the tissue or incision as the electrical cutting proceeds.

Presently, there is no known electrosurgical instrument that is pressure activated by a force exerted at the distal end of the instrument upon application to tissue or material.

SUMMARY OF THE INVENTION

The present invention is an RF electrosurgical instrument which is a pressure actuated device that can be either monopolar or bipolar. The device according to the present invention comprises a housing and a first connector in the housing for receiving RF electrical energy. A shaft assembly is movably connected to the housing. The shaft assembly includes at least one electrode at a distal of the shaft assembly. The shaft assembly also includes at least one conductive portion for passing the electrical energy to the at least one electrode. A spring is positioned between the shaft assembly and the housing for biasing the shaft assembly a distance away from the first connector. The distance defines a pre-determined gap between the first connector and the shaft assembly. The shaft assembly is proximally movable in the housing upon an application of force at the shaft assembly distal end for compressing the spring such that the at least one conductive portion traverses the pre-determined gap and contacts the first connector. Upon contacting the first connector, electrical energy is passed from the first connector to the electrode through the conductive portion.

The first connector is adjustably connected to the housing in order to adjust the pre-determined gap between the first connector and the shaft assembly. Alternatively, the first connector can remain fixed in the housing and the shaft assembly be adjustably connected or positioned in the housing.

An adjustment member, such as a rotation knob, is connected to the first connector for manually adjusting the pre-determined gap. The adjustment member also includes and indicator, such as an arrow, for aligning with a plurality of settings or gap adjustment markings, identified on an exterior surface of the housing at a proximal end of the housing. The settings may indicate the exact distance of the pre-determined gap at various settings or even indicate tissue type, surgical procedure, material, etc. that can be effectively energized with RF energy upon a requisite amount of force applied to the tissue, material, etc., at the distal end of the instrument.

Additionally, the shaft assembly includes a transfer shaft extending from the housing which serves as a first conductive portion of the shaft assembly. The shaft assembly also includes an outer shaft circumferentially surrounding the transfer shaft. The outer shaft is a second conductive portion of the shaft assembly.

As a monopolar device, a single electrode is located at the distal end of the shaft assembly. However, as a bipolar device, a first electrode is located at a distal end of the transfer shaft and a second electrode is located at a distal end of the outer shaft. An insulative barrier separates the first and second electrodes. Moreover, the distal end of the shaft assembly is made of an insulative material and both the first and second electrodes are exposed for transmitting bipolar RF energy therebetween. The first and second electrodes may comprise various configurations depending on the degree of therapy required at the tissue site.

In order to facilitate bipolar energy transmission, a second connector is located in the housing and operatively connected to the outer shaft for receiving and passing electrical energy from the second electrode. The spring is also made of a conductive material and circumferentially surrounds the transfer shaft in a spring housing located within the instrument housing. The spring is operatively connected between the outer shaft and the second connector.

Although the outer shaft is circumferentially spaced away from the transfer shaft, a longitudinal gap exists between the outer shaft and the transfer shaft. A plurality of insulative spacers are used in the gap between the shafts in order to maintain proper conductive pathways through the instrument.

It is an object of the present invention to provide an RF electrosurgical device that is a pressure activated device that delivers RF energy only upon a requisite amount of force being applied to the distal end of the instrument.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 8 is a perspective view of the distal end configuration of FIG. 1;

FIG. 9 is a perspective view of an alternate distal end configuration of FIG. 1 wherein one of the electrodes is oblong shape and the other electrode is circular in shape;

FIG. 10 is a perspective view of another alternate distal end configuration of FIG. 1 wherein both of the electrodes have an oblong shape;

FIG. 11 is a perspective view of yet another alternate distal end configuration of FIG. 1 wherein one electrode is circular in shape and the other electrode is a concentric ring; and FIG. 12 is a perspective view of the distal end of the instrument of FIG. 1 when the instrument is configured as a monopolar instrument.

DESCRIPTION OF THE PREFERRED EMBODIMENT

The present invention is a radio frequency (RF) electrosurgical instrument which is pressure activated or actuated. The present invention is useful for any type of surgical procedure that requires a certain degree of pressure to be placed against tissue or, a certain degree of pressure required to be placed directly on a material which is placed against tissue. Alternatively, the present invention, as a pressure actuation device, is useful for approximating and joining or adhering distinct layers of tissue. It is also useful for fastening or adhering a material such as a prosthetic, mesh, fastener, suspensory element, or the like directly to the tissue itself. The present invention will now be outlined in detail below.

Figure 1:
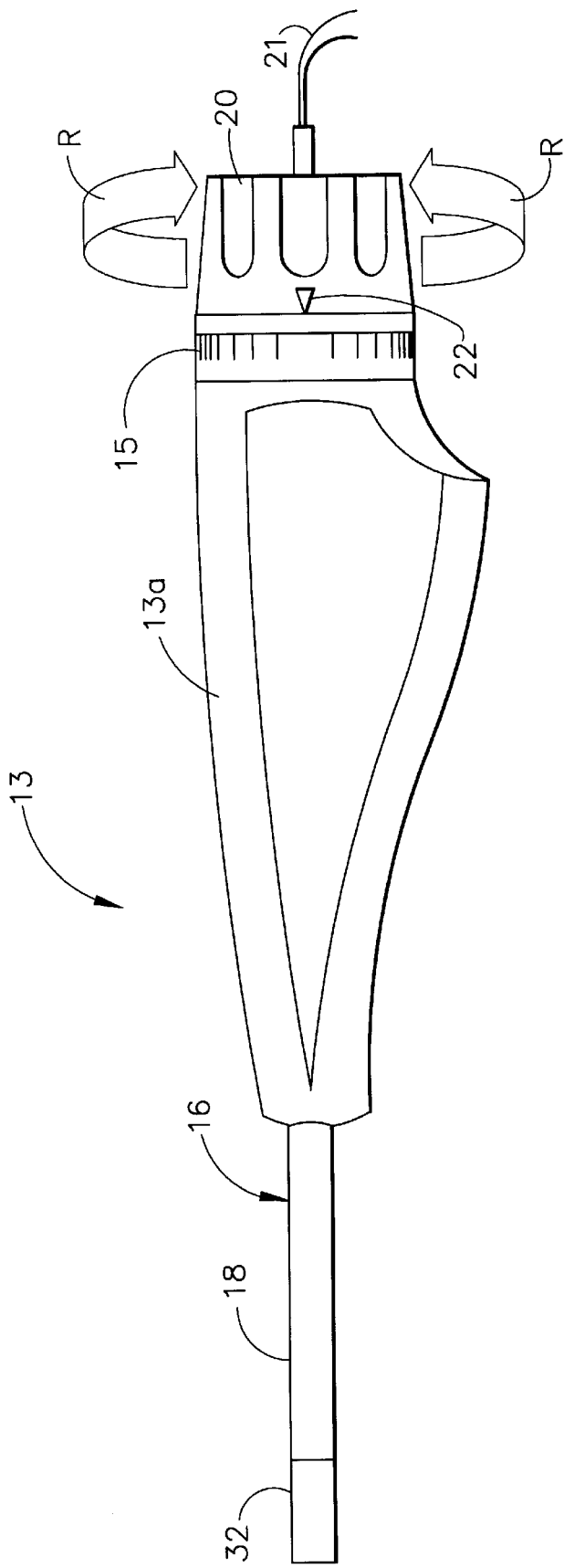
FIG. 1 is a side elevational view of an RF pressure instrument according to the present invention for use in a surgical procedure.

FIG. 1 illustrates the present invention as an RF electrosurgical instrument, generally designated 13, which can be either a bipolar or monopolar RF electrosurgical device. The electrosurgical instrument 13 is a pressure actuated device which includes a housing 13a and a shaft assembly, generally designated 16, extending from the housing 13a at the distal end of the housing 13a. The shaft assembly 16 includes an outer shaft 18 terminating with a tip 32 located at the distal end of the outer shaft 18. The outer shaft 18 is made of a conductive material with a non-conductive coating on an exterior surface thereof. The tip 32 is made of an insulating material. Both the shaft assembly 16 and the tip 32 will be described in greater detail below.

Additionally, the instrument 13 includes a gap adjustment member 20, which is a rotation knob or turning member, located at the proximal end of housing 13a. The gap adjustment member 20 is rotatable along directions R about the proximal end of the housing 13a. The gap adjustment member 20 also includes an indicator marking 22, such as an arrow, located on an exterior surface of the gap adjustment member 20. A plurality of pressure markings 15 are located on an exterior surface of the housing 13a at the proximal end of the housing 13a adjacent the gap adjustment member 20. The pressure markings 15 are a plurality of settings used to identify various pre-determined gap distances, pressures, tissue types, surgical procedures, or the like.

Since the gap adjustment member 20 is rotatable in any direction R at the proximal end of the housing 13a, one may manually adjust the gap adjustment member 20 such that the indicator 22 aligns with one of the various markings 15. A lead 21 is provided directly into the housing 13a through the gap adjustment member 20. The lead 21 is connected directly to an RF electrical power source and provides either monopolar or bipolar RF energy directly into the instrument 13.

Figure 2:
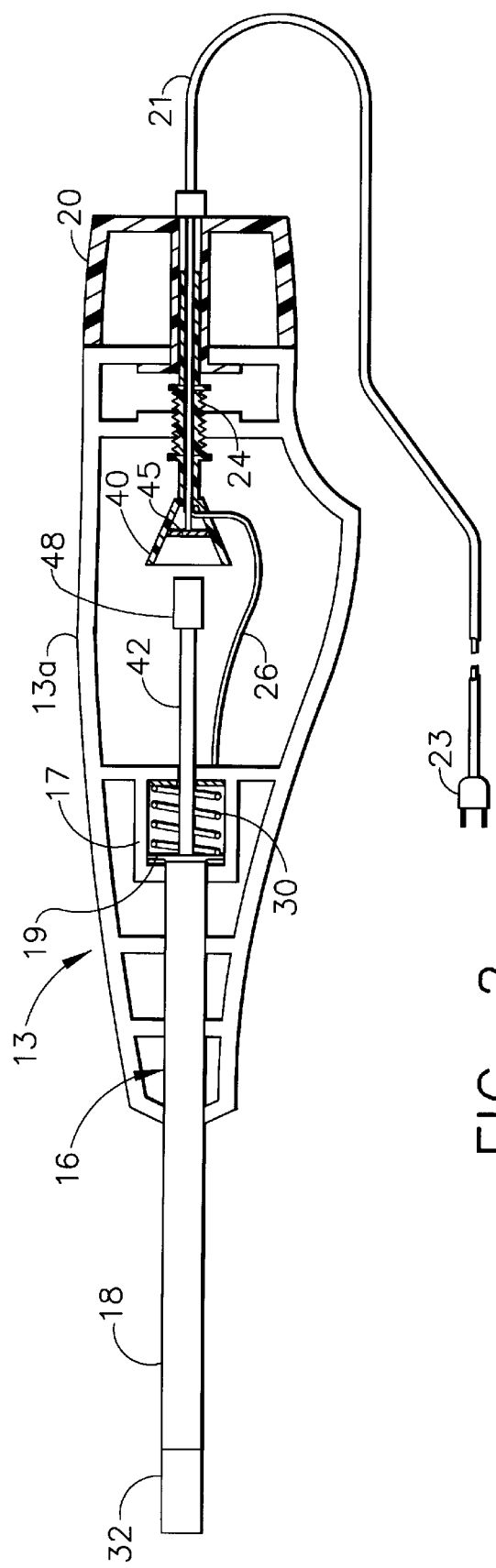
FIG. 2 is an upright section view of the instrument of FIG. 1 illustrating the instrument in a deactivation position or an "OFF" configuration.

FIG. 2 is an upright section view of the instrument 13 when the instrument 13 is in a deactivated or "OFF" configuration. Lead 21 also includes a plug 23 which is connected directly to the RF power source. Additionally, the lead 21 is connected directly to a first connector 24 which is a conductive element movably positioned in the housing 13a along the axis of the instrument 13. A second connector 26, which is also a conductive element, is also connected to the lead 21. Both the first connector 24 and second connector 26 transmit RF energy provided through the lead 21. As best shown, the first connector 24 and the second connector 26 are two separate elements responsible for providing an active pathway and a return pathway respectively as part of a bipolar circuit which will described in greater detail below.

The first connector 24 also includes a female receptacle 40, which is a conical-shaped hollow element. A contact face 45, which is also conductive, is located at the distal end of the first connector 24 within the female receptacle 40 itself.

The instrument 13 further includes a transfer shaft 42 terminating in male contact 48 located at a proximal end of the transfer shaft 42. The transfer shaft 42 and the male contact 48 are both made of a conductive material and constitute a first conductive portion of the shaft assembly 16.

A spring housing 17 is located in the instrument housing 13a and includes a compression spring 30 which is also made of a conductive material. The outer shaft 18 includes a shaft base 19 at a proximal end of the outer shaft 18 which contacts the compression spring 30 within the spring housing 17. The outer shaft 18 is a second conductive portion of the shaft assembly 16. As depicted, when the instrument 13 is in its deactivated or "OFF" position, the shaft assembly 16 is positioned such that the transfer shaft 42 is spaced away from the contact face 45 of the first connector 24. Moreover, in this configuration, the compression spring 30 is in a relaxed or uncompressed state.

Figure 3:
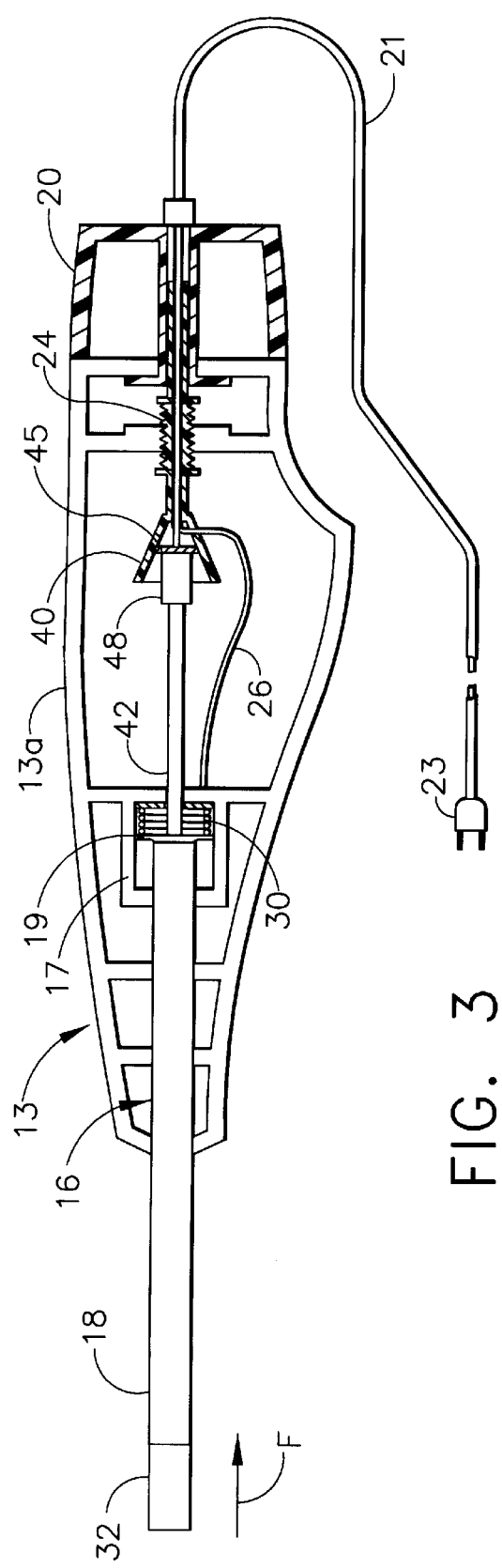
FIG. 3 is an upright section view of the instrument of FIG. 1 illustrating the instrument in an activated position or an "ON" configuration.

FIG. 3 is an upright section view of the instrument 13 depicting the instrument 13 in an activated position or an "ON" position. As best shown, upon an application of force F at the instrument tip 32, the shaft assembly 16 is moved proximally in the housing 13a such that the compression spring 30 is compressed by the outer shaft based 19 and male contact 48 of the transfer shaft 42 contacts the contact face 45 of the first connector 24 for providing a complete conductive pathway upon compression of the spring 30.

Figure 5:
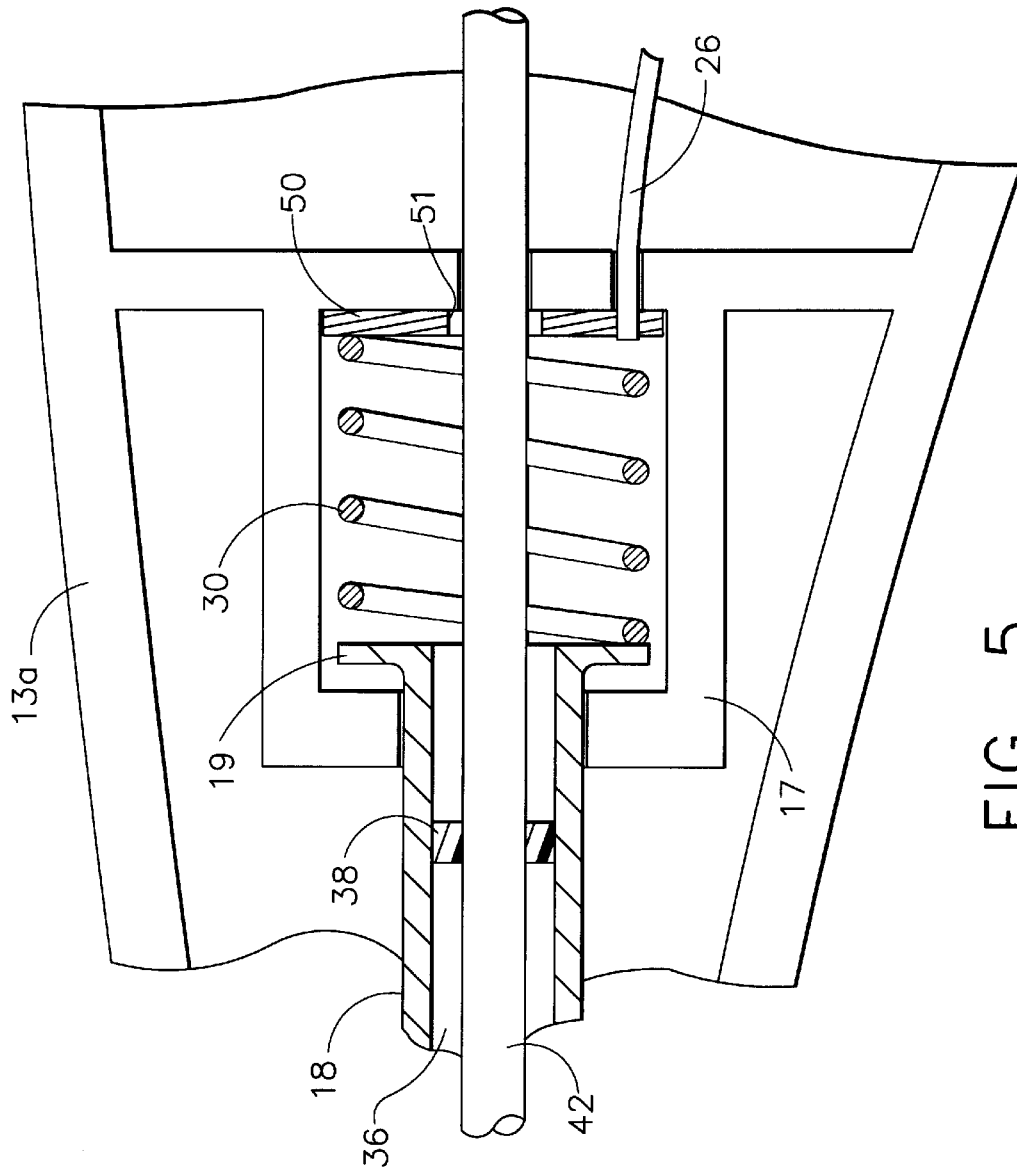
FIG. 5 is an enlarged fragmentary view in centerline upright section of the proximal end portion of the shaft assembly of the instrument of FIG. 1.
Figure 4:
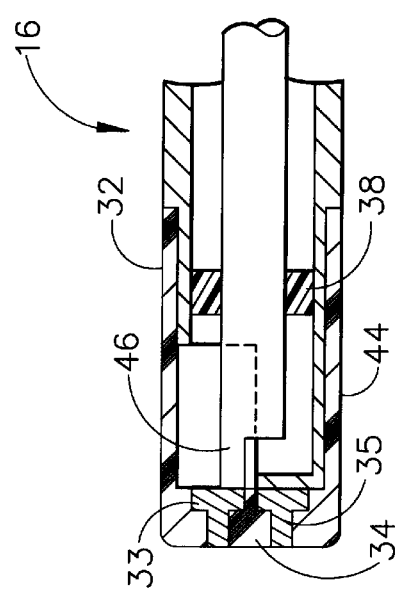
FIG. 4 is an enlarged fragmentary view in centerline upright section of the distal end of the instrument of FIG. 1.

Both FIG. 4 and FIG. 5 illustrate an enlarged fragmentary view in center line upright section of the distal end and proximal end of the shaft assembly 16 respectively. FIG. 5 shows the second connector 26 connected directly to a contact plate 50, which is also made of a conductive material, positioned in the spring housing 17. Moreover, the contact plate 50 includes a plate opening 51 for positioning of the transfer shaft 42. Furthermore, the compression spring 30 contacts both the outer shaft base 19 and the contact plate 50 to provide a conductive pathway therebetween. The compression spring 30 circumferentially surrounds the transfer shaft 42, but yet is spaced a sufficient distance from the transfer shaft 42 in order the avoid any overlap or sparking between respective conductive pathways defined by the first connector 24 and transfer shaft 42 relationship and the second connector 26 to contact plate 50, spring 30 and outer shaft base 19 relationship.

The transfer shaft 42 is axially positioned within the outer shaft 18 of the shaft assembly 16. The transfer shaft 42 is likewise sufficiently spaced from the outer shaft 18. This spacing defines a longitudinal gap 36 extending between outer shaft 18 and the transfer shaft 42. Accordingly, two distinct conductive pathways or portions exist at the shaft assembly 16, e.g. a first conductive portion or pathway which includes the transfer shaft 42 and a second conductive portion or pathway which includes the outer shaft 18. Insulative spacers 38 are provided between the transfer shaft 42 and the outer shaft 18 and positioned in the longitual gap 36. The insulative spacers 38 ensure separate conductive pathways of the outer shaft 18 and the transfer shaft 42 respectively.

Distal end 46 of transfer shaft 42 terminates in a first electrode 33. Distal end 44 of the outer shaft 18 terminates in a second electrode 35. The first electrode 33 and the second electrode 35 are separated by an insulated barrier 34. Both the first electrode 33 and the second electrode 35 are exposed at the distal end of the instrument 13 at the insulated tip 32. The term "exposed" as defined herein is intended to mean raised, flush, recessed or the like at the tip 32 of the instrument 13.

Figure 6:
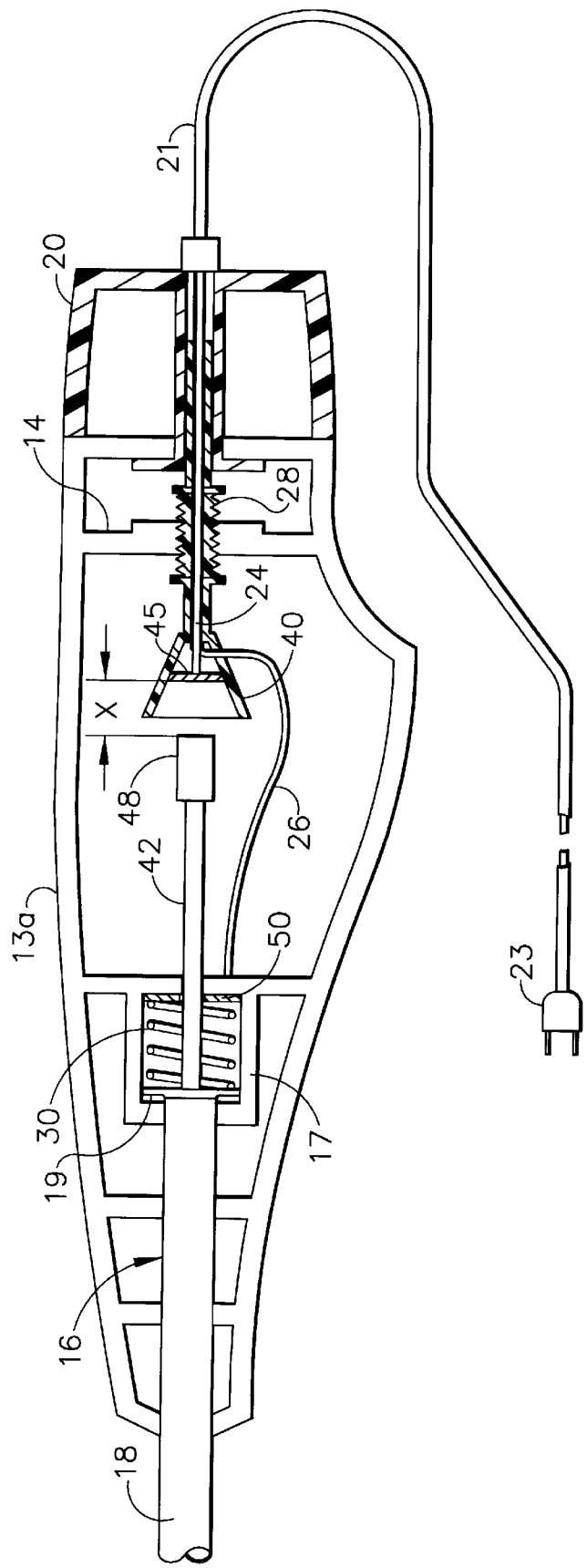
FIG. 6 is an enlarged fragmentary view of the handle housing of FIG. 2.

FIG. 6 is an enlarged fragmentary view of the handle housing 13a. As best shown, the first connector 24 includes a threaded portion 28 which is threadably moveable through internal rib 14 of the housing 13a. Gap adjustment member 20 is connected directly to the first connector 24 for threadably moving the first connector 24 proximally and distally through the internal rib 14 of the housing 13a upon manual rotation of the gap adjustment member 20 in rotation direction R (FIG. 1). As depicted, when the instrument 13 is in the deactivated or "OFF" position, transfer shaft 42 is spaced a distance away from the contact face 45 of the first connector 24. Accordingly, a pre-determined gap X is located between male contact 48 of the transfer shaft 42 and the contact face 45 of the first connector 24. The pre-determined gap distance X is a minimum distance required to be traversed upon force F being applied to the shaft assembly 16 at the tip 32 (FIG. 3). The pre-determined gap X also defines a minimum pressure value which is required in order compress spring 30 and traverse gap X. Although not shown, it is well within the scope of the present invention that the pre-determined gap X be maintained by providing a gap adjustment member in association with the shaft assembly 16 while the first connector 24 remains stationary. In essence, this is a reverse adjustment configuration to the arrangement illustrated in FIGS. 2,3,6, and 7.

Figure 7:
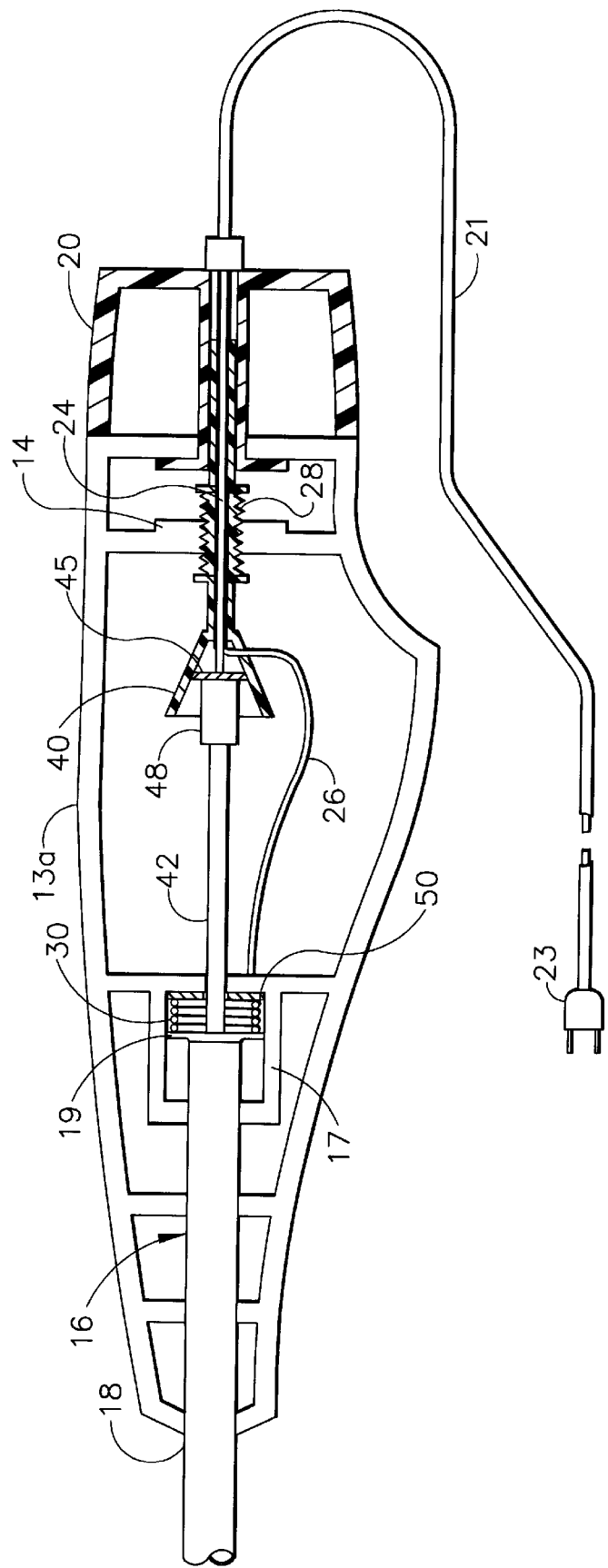
FIG. 7 is an enlarged fragmentary view of the handle housing of FIG. 3.

FIG. 7 is an enlarged fragmentary view of the handle housing 13a showing the transfer shaft 42 in engagement with the first connector 24 at the male contact 48 and contact face 45 resulting in the instrument 13 being activated. This allows RF energy to be delivered from a power source interfacing with plug 23 through lead 21 and into the instrument 13. In this configuration, the spring 30 is compressed as shown. The compression of the compression spring 30 allows the pre-determined gap or distance X to be traversed (FIG. 6) and results in a closed or completed circuit.

FIGS. 8 through FIG. 11 illustrate alternative embodiments of electrode arrangements when the present invention is a bipolar instrument. FIG. 8 shows that both the first electrode 33 and the second electrode 35 have a circular shape. FIG. 9 illustrates a second embodiment wherein a first electrode 33a has a circular shape and a second electrode 35a has an oblong shape. Both the first electrode 33a and the second electrode 35a are separated by insulative barrier 34a. FIG. 10 illustrates a third embodiment of the bipolar device according to the present invention having a first electrode 33b which has an oblong shape and a second electrode 35b also having a oblong shape wherein the first 33b and the second electrode 35b are separated by insulative barrier 34b. FIG. 11 shows a fourth embodiment of the bipolar device according to the present invention wherein a first electrode 33c has a circular shape and a second electrode 35c is a circumferential ring surrounding and spaced away from the first electrode 33c. The first electrode 33c and the second electrode 35c are separated by insulative barrier 34c.

FIG. 12 illustrates another embodiment of the present invention wherein the instrument 13 is a monopolar device having a single monopolar electrode 37 having a circular shape at the distal tip 32 of the instrument 13. It can be well appreciated by those of skill in the field that the monopolar electrode 37 may also include a plurality of contact points serving as a single pole. Although not shown, in order for one of ordinary skill to arrive at the monopolar device according to the present invention, one would eliminate the second connector 26 and maintain only the first connector 24. The modified instrument according to the present invention operates similar to the bipolar device disclosed herein. However, the reconfigured instrument 13, such as that described above, operates as a monopolar single pole device.

FIGS. 2,3,6 and 7 best illustrate the instrument 13 according to the present invention being used in operation. The first step prior to using the instrument 13 is for the surgeon to determine the type of surgical activity involved. This may include any type of surgical activity such as joining adjacent layers of tissue, joining mesh or a prosthetic to tissue, fastening tissue, suspending a suspensory element to tissue or the like. Once the type of surgical activity has been determined, the surgeon will locate a tissue site for applying the RF pressure instrument 13 according to the present invention.

Upon location of the tissue site, the surgeon manually adjusts the gap adjustment member 20 aligning the indicator marking 22 with the desired pressure or gap adjustment marking 15 such as depicted in FIG. 1. The gap adjustment member 20 is rotated in directions R in order achieve the surgeon's desired selection. Once the appropriate marking 15 has been selected, there remains a resulting pre-determined gap or distance X (FIG. 6) that is required to be traversed or overcome in order for the electrical circuit to be completed, e.g. through the contact between the transfer shaft 42 of the shaft assembly 16 to the first connector 24. At this point, the instrument 13 according to the present invention is still deactivated or in an "OFF" position and the electrical circuit is open.

The gap marking 15 is selected through the manual rotation R of the gap adjustment member 20 by the surgeon. By rotating in direction R, the first connector 24 is threadably positioned, either proximally or distally, at threaded portioned 28 and internal rib 14 of the housing 13a. The final positioning of the contact face 45 with respect to the contact member 48 of the transfer shaft 42 determines the gap or distance X.

After the appropriate pressure or gap marking 15 has been selected, the tip 32 of the instrument 13 is placed against tissue and pressure P is manually applied to the tissue by the surgeon holding handle housing 13a and exerting distal pressure to the tissue at the tip 32. Accordingly, upon applying pressure to the tissue, the resulting force F is applied through the shaft assembly 16 at the tip 32. The relationship of pressure P at the tissue to the force F exerted on the tip 32 is represented by formula:

$$P = F/A$$

Where P=the pressure exerted on the tissue or material; F=the proximal force exerted at the tip 32 of the instrument 13; and A=the total area of the tip 32 being applied against the tissue.

As force F is applied to the shaft assembly 16 at the instrument tip 32, the pre-determined gap X is gradually overcome by the transfer shaft 42 and the male contact 48 of the transfer shaft 42 contacts the face plate 45 of the first connector 24.

The amount force F necessary to overcome or traverse the pre-determined gap X relates to the formula:

$$F = kX$$

Where F=the force exerted at the instrument tip 32; k=the spring constant; and

X=the pre-determined gap or distance. Accordingly, the amount of force F necessary to overcome the pre-determined gap X is directly related to the characteristics of the spring, e.g. the spring constant k.

As illustrated in FIG. 7, once male contact 48 of the transfer shaft 42 contacts face plate 45 of the first connector 24, the circuit is closed or completed and RF energy is delivered from the power source through lead 21 to the contact of male connector 48 through the face plate 45. This allows RF energy to be passed directly to electrode 33. After which, RF energy is passed from electrode 33 through the tissue or material across barrier 34 to electrode 35. The electrodes 33 and 35 pass the RF energy therebetween as a bipolar configuration. Once the surgeon is satisfied that an appropriate amount of RF energy has been delivered to the tissue site, the instrument 13 is deactivated or moved to it's "OFF" position by ceasing the application of pressure P at the tissue with the tip 32 by withdrawing the tip 32 from the tissue site. The relief in pressure P enables the compression spring 30 to resume it's original position or uncompressed state and advance the shaft assembly 16 distally from the handle housing 13a.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical instrument comprising:
    a housing;
    a first connector in said housing for receiving electrical energy;
    a shaft assembly movably connected to said housing, said shaft assembly having at least one electrode at a distal end of said shaft assembly, said shaft assembly having at least one conductive portion for passing the electrical energy to said at least one electrode; and
    a spring positioned between said shaft assembly and said housing for biasing said shaft assembly a distance away from said first connector, said distance defining a pre-determined gap between said first connector and said shaft assembly, said shaft assembly being proximally movable in said housing upon an application of force at said shaft assembly distal end for compressing said spring such that said at least one conductive portion traverses the pre-determined gap and contacts said first connector for passing the electrical energy from said first connector to said at least one electrode through said at least one conductive portion and wherein either of said first connector or said shaft assembly is adjustably connected to said housing for adjusting said pre-determined gap between said first connector and said shaft assembly.

2. The electrosurgical instrument according to claim 1, wherein said first connector is adjustably connected to said housing.

3. The electrosurgical instrument according to claim 2, further including an adjustment member connected to said first connector for manually adjusting said pre-determined gap.

4. The electrosurgical instrument according to claim 3, wherein said adjustment member includes an indicator.

5. The electrosurgical instrument according to claim 4, wherein said housing includes at least one gap adjustment marking on an exterior surface thereof, said indicator of said adjustment member being alignable with said at least one adjustment marking for identifying at least one setting of said pre-determined gap.

6. The electrosurgical instrument according to claim 5, wherein said first connector is threadably connected to said housing.

7. The electrosurgical instrument according to claim 6, wherein said adjustment member is rotatable with respect to said housing.

8. The electrosurgical instrument according to claim 7, wherein said at least one conductive portion is a transfer shaft extending from said housing.

9. The electrosurgical instrument according to claim 8, wherein said shaft assembly also includes an outer shaft surrounding said transfer shaft.

10. The electrosurgical instrument according to claim 9, wherein said transfer shaft is a first conductive portion of said shaft assembly and said outer shaft is a second conductive portion of said shaft assembly.

11. The electrosurgical instrument according to claim 10, wherein said transfer shaft includes a first electrode at a distal end thereof.

12. The electrosurgical instrument according to claim 11, wherein said outer shaft includes a second electrode at a distal end thereof.

13. The electrosurgical instrument according to claim 12, further including a second connector in said housing for receiving electrical energy said second connector being operatively connected to the said outer shaft for passing said electrical energy to said second electrode.

14. The electrosurgical instrument according to claim 13, wherein said spring is made of a conductive material.

15. The electrosurgical instrument according to claim 14, wherein said spring is operatively connected between said outer shaft and said second connector.

16. The electrosurgical instrument according to claim 15, wherein said housing includes a spring housing for containing said spring therein.

17. The electrosurgical instrument according to claim 16, wherein said spring is circumferentially spaced from and surrounding said transfer shaft.

18. The electrosurgical instrument according to claim 17, wherein said transfer shaft is insulated from said outer shaft.

19. The electrosurgical instrument according to claim 18, further including at least one insulative spacer separating said transfer shaft from said outer shaft.

20. The electrosurgical instrument according to claim 19, wherein said first electrode is spaced from said second electrode, said first electrode being separated from said second electrode by an insulative barrier.

21. The electrosurgical instrument according to claim 20, wherein said distal end of said outer shaft is made of an insulated material.

22. The electrosurgical instrument according to claim 21, wherein said first electrode and said second electrode are exposed at said distal end of said shaft assembly.

23. The electrosurgical instrument according to claim 22, wherein either one of said first electrode and said second electrode have a circular shape.

24. The electrosurgical instrument according to claim 22, wherein said first electrode and said second electrode have a circular shape.

25. The electrosurgical instrument according to claim 23, wherein the other one of said first electrode and said second electrode has an oblong shape.

26. The electrosurgical instrument according to claim 22, wherein said first electrode and said second electrode have an oblong shape.

27. The electrosurgical instrument according to claim 22, wherein said first electrode has a circular shape and said second electrode is a circumferential ring surrounding said first electrode.

* * * * *